(12) United States Patent
Takuma

(10) Patent No.: US 8,231,607 B2
(45) Date of Patent: Jul. 31, 2012

(54) SUCTION CATHETER AND SUCTION-CATHETER SYSTEM

(76) Inventor: Norikata Takuma, Kokubunji (JP)

( * ) Notice: Subject to any disclaimer, the term of this patent is extended or adjusted under 35 U.S.C. 154(b) by 653 days.

(21) Appl. No.: 12/381,260

(22) Filed: Mar. 10, 2009

(65) Prior Publication Data
US 2010/0016785 A1 Jan. 21, 2010

(30) Foreign Application Priority Data
Jul. 18, 2008 (JP) .................. 2008-186974

(51) Int. Cl.
*A61M 1/00* (2006.01)
(52) U.S. Cl. ......... 604/540; 604/508; 604/128; 604/266
(58) Field of Classification Search .............. 604/540, 604/128–129, 266–268, 508–510
See application file for complete search history.

(56) References Cited

U.S. PATENT DOCUMENTS

| | | | |
|---|---|---|---|
| 6,805,692 B2 * | 10/2004 | Muni et al. ............. | 604/509 |
| 7,344,515 B2 | 3/2008 | Coyle | |
| 7,374,560 B2 * | 5/2008 | Ressemann et al. ....... | 604/509 |
| 7,422,579 B2 * | 9/2008 | Wahr et al. ............. | 604/509 |
| 2007/0293887 A1 | 12/2007 | Okushi et al. | |

FOREIGN PATENT DOCUMENTS

| | | |
|---|---|---|
| JP | 9-192230 | 7/1997 |
| JP | 2000-279525 | 10/2000 |
| JP | 2005-95410 | 4/2005 |
| JP | 2006-263125 | 10/2006 |
| JP | 2006-271693 | 10/2006 |
| JP | 2008-23318 | 2/2008 |
| JP | 2008-513111 | 5/2008 |

* cited by examiner

*Primary Examiner* — Lynne Anderson
(74) *Attorney, Agent, or Firm* — Jordan and Hamburg LLP

(57) ABSTRACT

Provided is a suction catheter including: a catheter main body made of a flexible lengthy body having a lumen inside; a leading-end case portion positioned at a leading-end portion of the catheter main body and including an opening for retrieving an object; and object cutting means partially exposed through the opening and movable in the axial direction within the leading-end case portion. The object cutting means includes a cutting portion exposed through the opening portion, and a power receiving portion driving the cutting portion when receiving power from outside. A leading-end side of the suction catheter is inserted into a blood vessel while a base-end portion of the suction catheter is connected to a suction apparatus. An object sticking to the internal wall of the blood vessel is cut off by operating the object cutting means in the opening of the leading-end case portion while the lumen is vacuumed. The cut-off object is immediately sucked in and retrieved.

20 Claims, 9 Drawing Sheets

RELATED ART

SUCTION CATHETER AND SUCTION-CATHETER SYSTEM

BACKGROUND OF THE INVENTION

1. Field of the Invention

The present invention relates to a suction catheter used in a treatment where the suction catheter is inserted into a blood vessel to suck out and remove an object such as a blood clot therefrom. Specifically, the present invention relates to a technique that is used when objects cause an occluded blood-vascular system, such as in the case of cerebral infarction or myocardial infarction, for the purpose of retrieving and removing the objects, easily and smoothly, from the blood vessel without allowing the objects to flow down the stream.

2. Description of the Related Art

A number of diseases are known to be caused by an occluded blood vessel. For example, each of the cerebral infarction and the myocardial infarction is a disease caused by an occluded arterial system of the corresponding organ. An economy-class syndrome is a potentially fatal disease that is caused by an occluded pulmonary blood vessel due to a blood clot formed in a leg vein.

The blood clot formed in a blood vessel is conventionally removed by use of an apparatus inserted into the blood vessel mainly in accordance with any one of the following two known methods. In one method, an object, such as a blood clot, is removed by being sucked out with the opening at the leading end of the suction catheter being brought into direct contact with the object. In the other method, the blood clot is firstly fractured, and the fractured fragments of the blood clot are then sucked out by the suction catheter.

For example, the following techniques have been proposed. A suction catheter employed in a proposed technique includes: a catheter main body to be inserted into the blood vessel; and a vibrator that makes the catheter main body vibrate. The vibrating catheter main body is brought into contact with a blood clot, and thus the blood clot is gradually fractured from the surface. According to this technique, the blood clot can be quickly removed without damaging the blood vessel. For more detail, see Japanese Patent Application Publication No. 2005-95410 (Patent Document 1).

A suction catheter employed in another proposed technique includes an actuator provided near the leading end of the catheter. When the actuator is made to vibrate, the vibration in turn makes the leading end of the catheter vibrate. The leading end of the vibrating catheter or an irregular face formed at the leading end is used for chipping away the adjacent objects. For more detail, see Japanese Patent Application Publication No. Hei 9-192230 (Patent Document 2).

FIG. 13 shows a suction catheter 100 employed in still another proposed technique. The suction catheter 100 includes an obliquely-formed leading-end portion 101a. The leading-end portion 101a is brought into contact with the object, such as a blood clot, while the inside of a lumen 111 of a catheter main body 101 is being vacuumed. Thus, the object is removed by the sucking force. An example of the suction catheter of this type is a blood-clot suction catheter that is commercially available under the registered trade name Thrombuster from Kaneka Medix Corp. Another example of the type of suction catheter is a catheter for removing embolus in the central circulatory system that is commercially available under the registered trade name Eliminate from Clinical Supply Co., Ltd.

A suction catheter employed in still another proposed technique includes a taper-shaped spiral portion provided at a leading-end portion of the suction catheter main body. The spiral portion has a coil-shaped piece wound up by at least one turn. A catheter for fracturing objects is disposed inside the spiral portion, and ejects a jet stream of a liquid to fracture an object (for example, a blood clot) in the blood vessel. The object thus fractured is then sucked up from the leading-end portion of the catheter, and is taken to the outside. For more detail, see Japanese Patent Application Publication No. Hei 2006-271693 (Patent Document 3).

A suction catheter employed in still another proposed technique includes a tubular body that has an opening for ejection and an opening for suction. To dissolve an object to be dissolved, a dissolving agent is ejected out from the opening for ejection to the object to be dissolved. Parts of the object to be dissolved may remain un-dissolved. Such fine fragments of the object to be dissolved are sucked into the tubular body from the opening for suction. In addition, mechanical means for generating vibrations is provided to the tubular body so as to fracture the object to be dissolved. With the suction catheter described above, fine fragments of a blood clot that has been fractured and left undissolved are sucked into the tubular body from the opening for suction. For more detail, see Japanese Patent Application Publication No. 2006-263125 (Patent Document 4).

A suction catheter employed in still another proposed technique is provided with a vibrator. An irregular-surface portion is formed in the outer circumferential surface of the leading-end portion of the suction catheter. The vibrator makes the irregular-surface portion vibrate, and the vibrating irregular-surface portion chips away the atheroma formed in the arteriosclerotic narrowed lesion. The chipped fragments of the atheroma is sucked from the opening portion for suction at the leading-end portion of the catheter, and taken out of the body. For more detail, see Japanese Patent Application Publication No. 2000-279525 (Patent Document 5).

Neither the means disclosed in Patent Document 1 nor the means disclosed in Patent Document 2 has an enough ability to easily and smoothly remove a blood clot. Likewise, the product with an obliquely-formed leading-end portion does not have an enough ability to easily and smoothly remove a blood clot.

In all of the means disclosed in Patent Documents 3 to 5, the position where the blood clot is subjected to fracturing or the like is away from the position where the blood clot is to be retrieved. For this reason, when the direction of blood flow is not favorable, the fragments of the blood clot may possibly flow away down the stream. For example, when a blood clot is removed from a blood vessel located in the head, the catheter has to be inserted from the upstream side of the blood clot in the direction of blood flow. Accordingly, the fragments of the blood clot readily flow away down the stream unless the fragments of the blood clot are retrieved substantially at the same time of the fracturing or the like. When the original blood clot is formed in an arterial system, the fragments of the blood clot that have flowed down the stream may cause a new blood clot to be formed in a peripheral capillary.

The description given thus far reveals some of the requirements for a suction catheter used for sucking and removing an object, such as a blood clot, formed inside a blood vessel. What follows are some examples of such requirements.

1) To have an enough ability to remove the blood clot.
2) To be capable of preventing the blood-clot fragments from flowing down the stream.
3) To allow the cutting and the suction of the blood clot to be carried out safely.
4) To follow the complex bending of the blood vessel.

None of the suction catheters that have been proposed thus far satisfies all the above-mentioned requirements. Accordingly, what has been longed for is a proposal for a suction catheter that is capable of retrieving and removing, easily and smoothly, an object, such as a blood clot, formed inside a blood vessel from the blood vessel without allowing the flowing-away of the object down the stream.

SUMMARY OF THE INVENTION

The above-described circumstances have led us to make the present invention. Accordingly, an object of the present invention is to provide a suction catheter that is capable of retrieving and removing, easily and smoothly, an object, such as a blood clot, formed inside a blood vessel from the blood vessel without allowing the flowing-away of the object down the stream. Another object of the present invention is to provide a suction-catheter system that allows the above-mentioned suction catheter to operate efficiently.

To achieve the above-mentioned objects, an aspect of the present invention provides a suction catheter made of a flexible lengthy body with a lumen formed in the flexible lengthy body, and used in a treatment where a leading-end side of the suction catheter is inserted into a blood vessel, where a base-end portion is connected to a suction apparatus, and where the lumen is vacuumed by means of the suction apparatus so as to suck out and retrieve an object in the blood vessel. The provided suction catheter includes a catheter main body, a leading-end case portion, and object cutting means. The catheter main body is made of the lengthy body. The leading-end case portion is positioned at a leading-end portion of the catheter main body and includes an opening for retrieving the object. The object cutting means is partially exposed through the opening, and is movable in the axial direction within the leading-end case portion. In addition, the object cutting means includes a cutting portion and a power receiving portion. The cutting portion includes a cutting area made of a wire-like member provided so as to traverse in a substantially perpendicular direction to the axial direction. The power receiving portion is connected to the cutting portion and moves the cutting portion in the axial direction when the power receiving portion receives power from outside. While the object cutting means is in operation, the object that sticks to an internal wall of the blood vessel is cut off, at the opening of the leading-end case portion, by means of the cutting area of the cutting portion.

In addition, it is preferable that, in the suction catheter, the cutting portion be a spiral body formed by winding up the wire-like member a number of times.

In addition, it is preferable that, in the suction catheter, the leading-end case portion include a locking stopper formed in an internal wall of the leading-end case portion. The locking stopper is designed to restrict a movement of the object cutting means toward the base-end portion of the catheter main body.

In addition, it is preferable that, in the suction catheter, either at least a part of the leading-end case portion or at least a part of the object cutting means be made of a metal member.

In addition, it is preferable that, in the suction catheter, the opening be formed in a leading-end inclined face of an obliquely-formed leading-end portion of the leading-end case portion.

In addition, it is preferable that, in the suction catheter, the opening be formed in a leading-end-side circumferential-body surface of the leading-end case portion.

In addition, it is preferable that, in the suction catheter, the power receiving portion be made of a magnetic material, and that the leading-end case portion includes magnetic-force generating means for supplying power to the power receiving portion. The magnetic-force generating means is provided to the internal wall of the leading-end case portion.

In addition, it is preferable that, in the suction catheter, at least one of the catheter main body and the leading-end case portion includes a guide-wire hole formed in the outer surface thereof. The guide-wire hole allows a guide wire to be inserted thereinto.

In addition, another aspect of the present invention provides a suction-catheter system that includes: the above-described suction catheter; and driving means for supplying power to the object cutting means included in the suction catheter.

In addition, it is preferable that, in the suction catheter system, the driving means be capable of adjusting the strength of the power supplied to the object cutting means.

In addition, it is preferable that, in the suction catheter system, the object cutting means include a stretchable member that enables the object cutting means to move back and forth in response to the change in the strength of the power supplied by the driving means, and that the driving means be a suction apparatus that attracts the object cutting means by means of a sucking force.

In addition, it is preferable that, in the suction catheter system, at least a part of the object cutting means be made of a magnetic material, and that the driving means be a magnetic-force apparatus that attracts or repels the object cutting means by means of a magnetic force.

In the suction catheter provided according to the aspects of the present invention, the leading-end case portion with an opening for retrieving an object in a blood vessel is positioned at the leading-end portion of the catheter main body that is made of a flexible lengthy body with a lumen formed therein. The suction catheter includes the object cutting means that is partially exposed through the opening and is movable, within the leading-end case portion, in the same direction as the direction of the longitudinal axis of the catheter main body. Accordingly, the position where the object is cut off by means of the object cutting means and the position of the opening where the object thus cut off is retrieved within the blood vessel are not away from each other. Rather, the suction catheter has a structure in which the above-mentioned two positions can be made substantially the same. Accordingly, the cutting operation, which is performed at the opening of the leading-end case portion by means of the object cutting means in operation, to cut the object sticking to the internal wall of the blood vessel and the sucking operation to take the cut-off object into the leading-end case portion from the opening as quickly as possible can be processed in an almost simultaneous parallel fashion.

For this reason, the aspects of the present invention can provides a suction catheter that is capable of retrieving and removing, easily and smoothly, an object, such as a blood clot, formed inside a blood vessel from the blood vessel without allowing the flowing-away of the object down the stream.

BRIEF DESCRIPTION OF THE DRAWINGS

FIG. 1A is a schematic sectional view illustrating the suction catheter before its cutting action. FIG. 1B is a schematic sectional view illustrating the suction catheter after its cutting action.

FIG. 2A is a schematic sectional view illustrating the state before a sucking force is supplied. FIG. 2B is a schematic sectional view illustrating the state where a strong sucking force is supplied. FIG. 2C is a schematic sectional view illustrating the state where a weak sucking force is supplied instead of the strong sucking force.

FIG. 3A is a schematic sectional view illustrating the state where the suction catheter is inserted into a blood vessel. FIG. 3B is a schematic sectional view illustrating the state where a leading-end face of the suction catheter is brought into contact with the blood clot. FIG. 3C is a schematic sectional view illustrating the state where blood clot is cut by means of the object cutting means and the resultant fragments of the blood clot are retrieved.

FIG. 4A is a schematic sectional view illustrating the state where the retrieval channel is fully opened. FIG. 4B is a schematic sectional view illustrating the state where the retrieval channel is partially closed with a power receiving portion of the object cutting means.

DETAILED DESCRIPTION OF THE INVENTION

Some exemplary embodiments of the present invention will be described below with reference to the drawings.

Note that the embodiments described below are preferred specific examples with various technical limitations. However, the embodiments with such limitations are not the only forms representing the scope of the present invention unless a specific remark to the effect that the present invention is limited in a described way is given in the following description.

A suction catheter to be provided according to the present invention is assumed to be used in the following treatment. The leading-end side of the suction catheter is inserted into a blood vessel while the base-end portion of the suction catheter is connected to a suction apparatus. The lumen is vacuumed by means of this suction apparatus, so that the object inside the blood vessel can be sucked out and retrieved.

To put it differently, the suction catheter of the present invention is used together with suction means (a suction apparatus). When an object causes an occluded blood-vascular system, such as in the case of cerebral infarction or myocardial infarction, the suction catheter is inserted deeply into the blood vessel until the suction catheter can reach the lesion. An object, such as a blood clot, that causes the occlusion of the blood vessel (hereafter, such an object will be simply referred to as a "blood clot") is sucked directly by the suction catheter, and is thus removed out of the body. Note that the suction apparatus to be used in the following embodiments is an ordinary suction apparatus that is commonly used in the above-mentioned treatment. Accordingly, no description of the suction apparatus will be given in the following embodiments.

First Embodiment

Figure 1A:
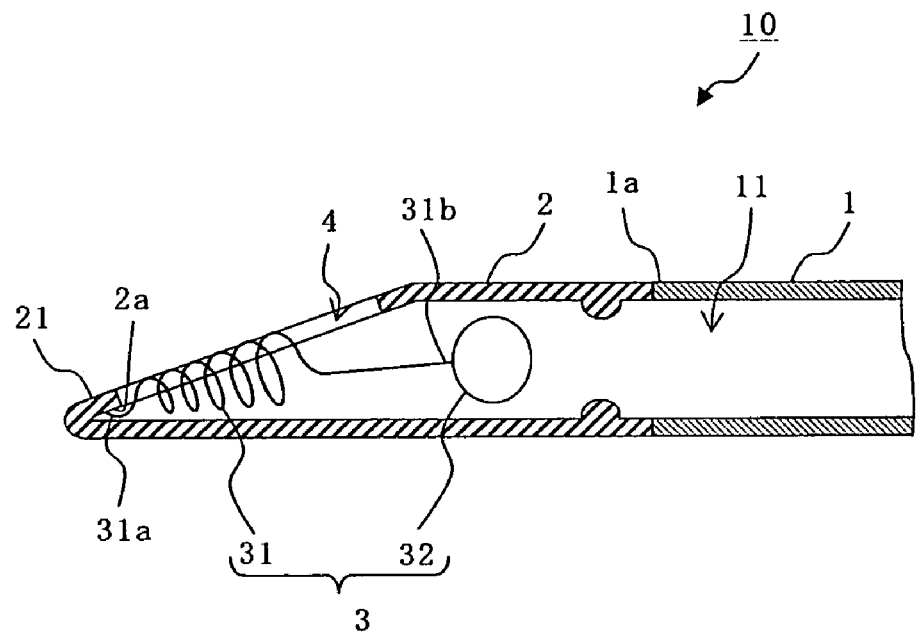
FIGS. 1A and 1B are drawings each of which illustrates a suction catheter according to a first embodiment of the present invention.
Figure 1B:
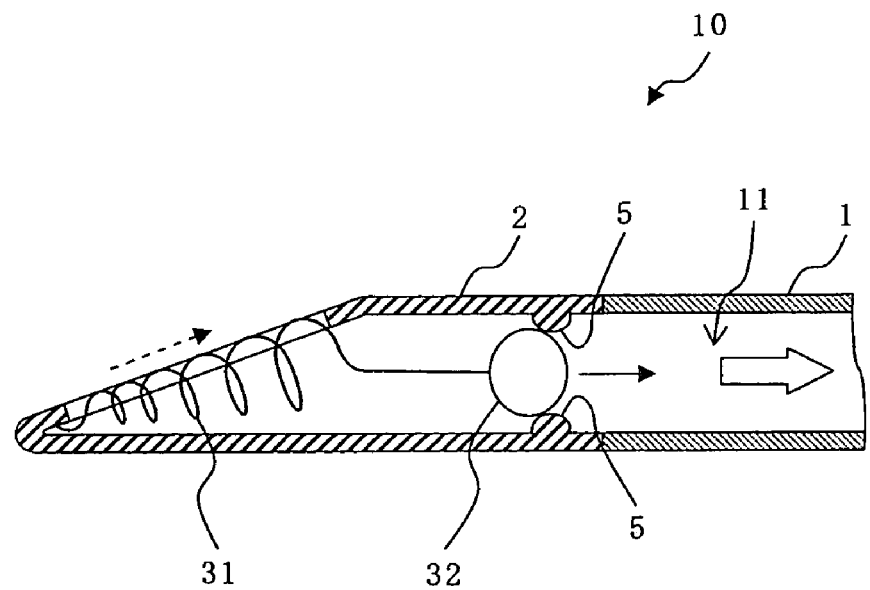

FIGS. 1A and 1B are drawings each of which illustrates a suction catheter according to the present invention. FIG. 1A is a schematic sectional view illustrating the suction catheter before its action. FIG. 1B is a schematic sectional view illustrating the suction catheter after its action.

As FIGS. 1A and 1B show, a suction catheter 10 according to this first embodiment includes: a catheter main body 1; a leading-end case portion 2 positioned at a leading-end portion 1a of the catheter main body 1; and object cutting means 3 installed in the leading-end case portion 2.

The catheter main body 1 is a flexible lengthy body with a lumen 11 formed inside the main body. The catheter main body 1 with such a structure is capable of following sufficiently the bending of the blood vessel.

The catheter main body 1 can be made of various materials. Some examples of such materials are: polyvinyl chloride; polyethylene; polypropylene; polyurethane; ethylene-propylene copolymer; ethylene-vinyl acetate copolymer; other polyolefins; polyethylene terephthalate; polybutylene terephthalate; other polyesters; polyamide; polyimide; polytetrafluoroethylene; polyvinylidene-fluoride; other fluorinated resins; various other thermoplastic resins; various other thermosetting resins; polyamide elastomer; polyester elastomer; other thermoplastic elastomers; and various rubbers.

The outer diameter of the catheter main body 1 is not limited to a certain range. The outer diameter of the catheter main body 1 is preferably made as small as possible in the interest of removing a blood clot formed in a capillary. A preferable outer diameter of the catheter main body 1 is, for example, approximately 1 mm.

An opening 4 is formed in the leading-end case portion 2, and the blood clot is retrieved through the opening 4. The opening 4 also serves as the inlet through which the blood clot is sucked into the vacuumed lumen 11 of the catheter main body 1. Accordingly, the opening 4 is formed so as to face the blood clot that sticks to the internal wall of the blood vessel.

As FIGS. 1A and 1B show, the leading-end portion of the leading-end case portion 2 is formed obliquely to be a leading-end inclined face 21, and the opening 4 is formed in the leading-end inclined face 21.

The leading-end case portion 2 may be formed either integrally with or separately from the catheter main body 1.

A part of the object cutting means 3 is exposed through the opening 4. In addition, the object cutting means 3 is movable in the axial direction within the leading-end case portion 2. Note that "the axial direction" mentioned here is the same direction as the direction of the longitudinal axis of the catheter main body 1.

The object cutting means 3 includes, for example, a cutting portion 31 that is exposed through the opening 4, and a power receiving portion 32 which receives the power from outside and which moves the cutting portion 31.

Accordingly, the use of the suction catheter 10 requires driving means to give the power to the power receiving portion 32 of the object cutting means 3. Combining the suction catheter 10 and the driving means (not illustrated) together forms a suction catheter system in the present invention.

The cutting portion 31 may be made of a wire-like member that is provided so as to traverse in a substantially perpendicular direction to the axial direction in which the object cutting means 3 is movable. The direction that is substantially perpendicular to the movable direction for the object cutting means 3 can be understood as follows. When moving along with the movement of the object cutting means 3, the cutting portion 31 draws a plane trajectory in the above-mentioned direction.

In addition, the cutting portion 31 is formed so as to have a retrieving opening for readily taking the blood clot that has been cut into the inside of the leading-end case portion 2.

Some examples of the cutting portion 31 formed by a wire-like member with a retrieving opening are: an arch-shaped body with a wire-like member with only one cutting region formed; and a spiral body formed by winding up, a number of times, a wire-like member with gaps between two adjacent lines so as to form plural cutting areas. Note that the wire-like member portion is provided so as to traverse in a substantially perpendicular direction to the axial direction in which the object cutting means is movable. Accordingly, when the cutting portion 31 is made of the arch-shaped body and the spiral body, the wire-like member portion provided in the above-mentioned way has an arc shape that resembles the shape of the internal wall of the blood vessel. The cutting portion 31 with the above-described form can remove efficiently the blood clot.

In FIGS. 1A and 1B, the cutting portion 31 is illustrated as a spiral-shaped body (coil-spring shape). The spiral-shaped cutting portion 31 has a first end 31a fixed to the proximity of an internal leading end 2a of the leading-end case portion 2, and a second end 31b provided with the power receiving portion 32.

An example of an external power to move the power receiving portion 32 is the sucking force to attract the power receiving portion 32. The use of sucking force as the power used for the above-mentioned purpose allows a suction apparatus (not illustrated) used for vacuuming the lumen 11 of the catheter main body 1 and for sucking and retrieving the blood clot to be also used as the source of sucking force. Accordingly, no additional driving means for giving power needs to be provided, so that the fracturing of and the retrieving of the blood clot can be carried out economically and with efficiency both in design and in operation.

Incidentally, the use of the sucking force as the power to attract the power receiving portion 32 allows the power receiving portion 32 to be formed as a spherical voluminous portion attached to the second end of the spiral-shaped cutting portion 31.

Now, suppose a case where the suction apparatus (not illustrated) is used for vacuuming the lumen 11 of the catheter main body 1 of the suction catheter 10 of this embodiment shown in FIG. 1A. In this case, a sucking force indicated by the outline arrow in FIG. 1B is produced. Accordingly, the power receiving portion 32 is supplied with a power, and moves in the direction indicated by the solid-line arrow. In addition, along with the movement of the power receiving portion 32, the cutting portion 31 stretches out in the direction indicated by the dot-line arrow so as to widen the distances between adjacent sections of the wire-like member of the cutting portion 31.

Figure 2A:
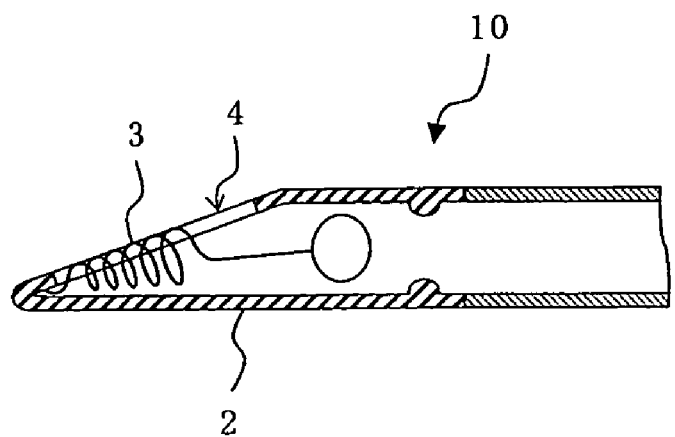
FIGS. 2A, 2B, and 2C are drawings illustrating a series of actions of object cutting means of the suction catheter according to the first embodiment of the present invention.
Figure 2B:
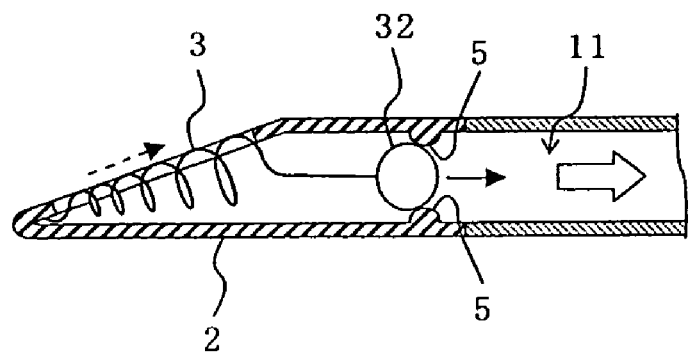
Figure 2C:
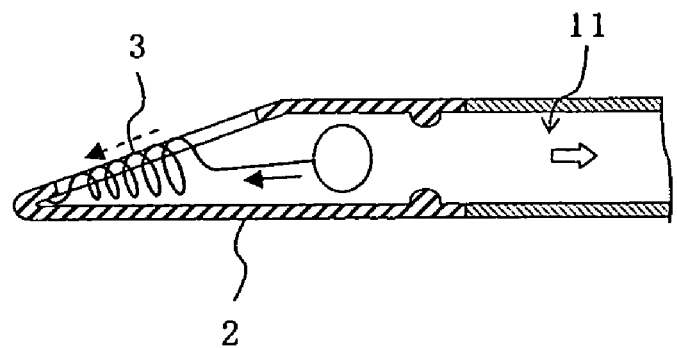

In addition, when the cutting portion 31 is formed as a spiral body in this embodiment, the spring elastic force of the cutting portion 31 allows the object cutting means 3 to move back and forth as FIGS. 2A, 2B, and 2C show. FIGS. 2A, 2B, and 2C are drawings illustrating a series of actions of the object cutting means 3 in the suction catheter 10.

The back-and-forth motion of the object cutting means 3 can be achieved by adjusting the strength of the power in the driving means for giving power to the power receiving means 32. In this embodiment, the power strength is adjusted by making the sucking pressure stronger or weaker.

To be more specific, while the driving means (not illustrated) is not in operation, the suction catheter 10 stays in a state where the cutting portion 31 is contracted toward the internal leading end 2a of the leading-end case portion 2 as FIG. 2A shows.

When the driving means give a strong sucking force to the power receiving portion 32, the power receiving portion 32 is pulled toward the side of the base-end portion of the catheter main body 1, and the cutting portion 31 stretches out along with the movement of the power receiving portion 32 as FIG. 2B shows.

When the driving means stops its operation or when the sucking force of the driving means is weakened, the power receiving portion 32 is pulled back to the side of the internal leading end 2a of the leading-end case portion 2 by the spring biasing force that is inherent in the cutting portion 31. This is the state that FIG. 2C shows.

Note that what makes the back-and-forth motion of the object cutting means 3 possible in this embodiment is the spring elastic force inherent in the cutting portion 31 that is formed as a spiral body. In contrast, when the object cutting means is not stretchable, a separate stretcher portion has to be provided.

As FIGS. 1A and 1B, and 2A to 2C show, locking stoppers 5 and 5 are formed in the internal wall of the leading-end case portion 2 in this embodiment. The locking stoppers 5 and 5 are designed to restrict the movement of the power receiving portion 32 toward the side of the base-end portion of the catheter main body 1. The locking stoppers 5 and 5 prevent the power receiving portion 32 from being pulled an unnecessarily long distance, so that an efficient and smooth back-and-forth motion of the object cutting means 3 can be achieved.

Note that the locking stoppers 5 and 5 may be formed integrally with the leading-end case portion 2 or may be formed separately from the leading-end case portion 2 and attached thereto.

Figure 3A:
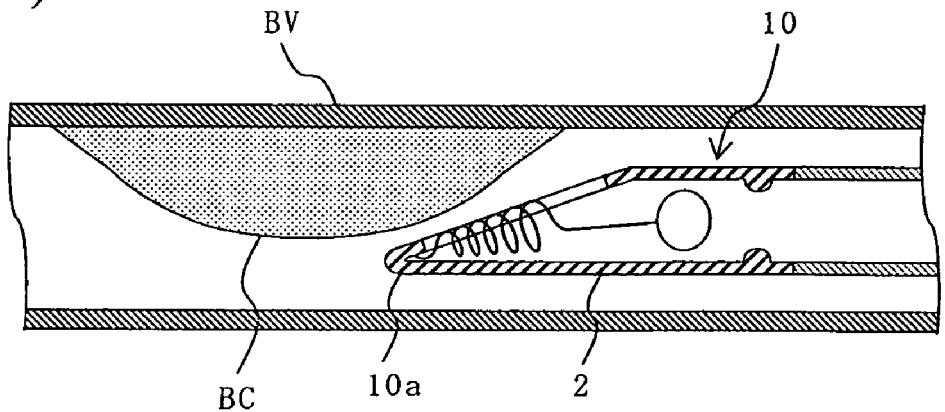
FIGS. 3A, 3B, and 3C are schematic sectional views illustrating a series of steps for cutting and removing an object (a blood clot) by means of a suction catheter according to the first embodiment of the present invention.
Figure 3B:
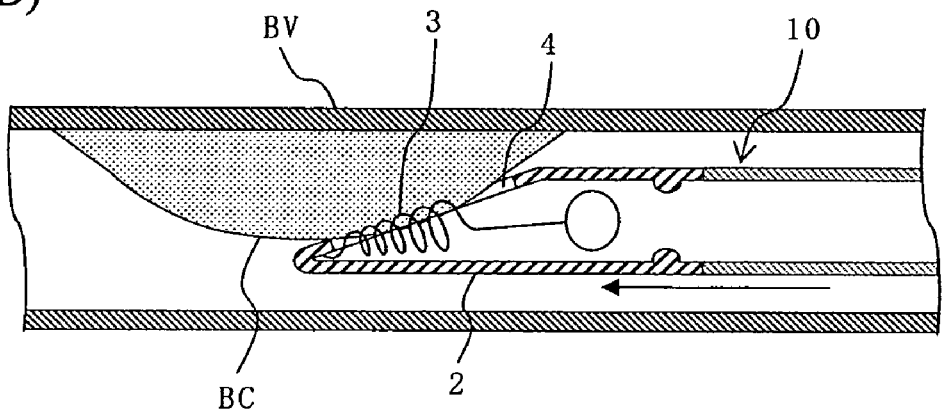
Figure 3C:
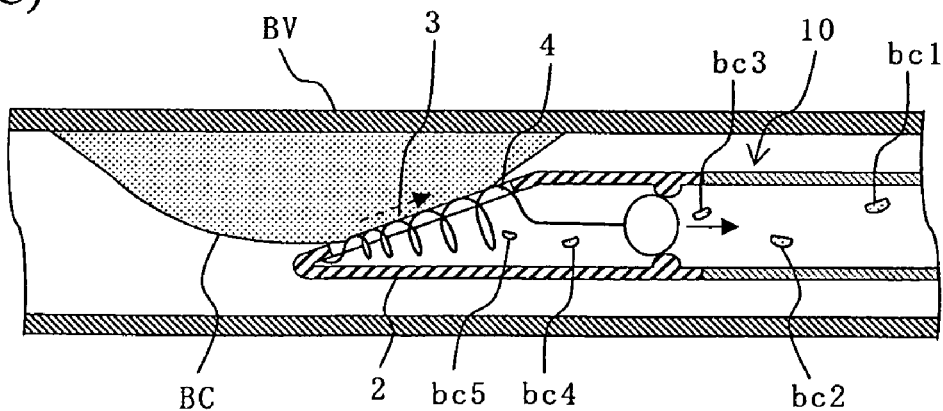

What will be described next is a way of cutting and removing a blood clot in a blood vessel by means of the suction catheter 10 with the above-described configuration. FIGS. 3A, 3B, and 3C are schematic sectional diagrams illustrating a series of steps for cutting and removing a blood clot by means of a suction catheter.

Firstly, as FIG. 3A shows, the suction catheter 10 is inserted into a blood vessel BV until a leading-end side 10a of the suction catheter 10 reaches a blood clot BC. In the meanwhile, the base-end portion of the suction catheter 10 is connected to a suction apparatus.

Then, as FIG. 3B shows, the cutting portion 31 of the object cutting means 3 exposed through the opening 4 of the leading-end case portion 2 is brought into contact with the blood clot BC.

Subsequently, as FIG. 3C shows, the lumen 11 is vacuumed by means of the suction apparatus, and the object cutting means 3 is made to move back and forth. The blood clot BC in the blood vessel BV is thus cut by the cutting portion 31, and the fragments of the blood clot BC are securely sucked in, and caught, and then are retrieved. FIG. 3C shows how five fragments bc1, bc2, bc3, bc4, and bc5 that are cut from the blood clot BC are sucked and retrieved.

Figure 4A:
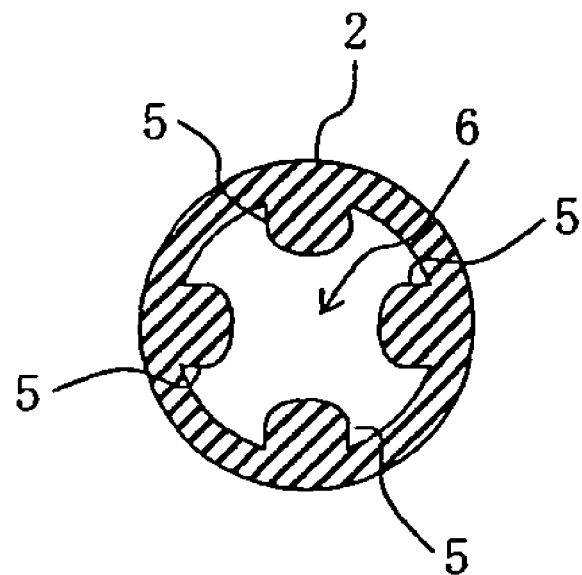
FIGS. 4A and 4B are drawings each of which illustrates a retrieval channel for the object (the blood clot) formed in the suction catheter according to the first embodiment of the present invention.

In addition, as FIG. 4A shows, the plural bump-shaped locking stoppers 5 and 5 are formed so as to protrude from some parts of the internal wall surface of the leading-end case portion 2. The rest of the leading-end case portion 2 serves as a retrieval channel 6 used when the fragments of the blood clot BC are sucked and retrieved. Now, suppose a case where a single annular locking stopper 5 is formed with a uniform height (thickness) all along the circumference of the internal wall of the leading-end case portion 2. In this case, when the power receiving portion 32 pulled toward the base-end portion side of the catheter main body 1 is brought into contact with the locking stopper 5, the power receiving portion 32 may possibly close the retrieval channel 6.

Figure 4B:
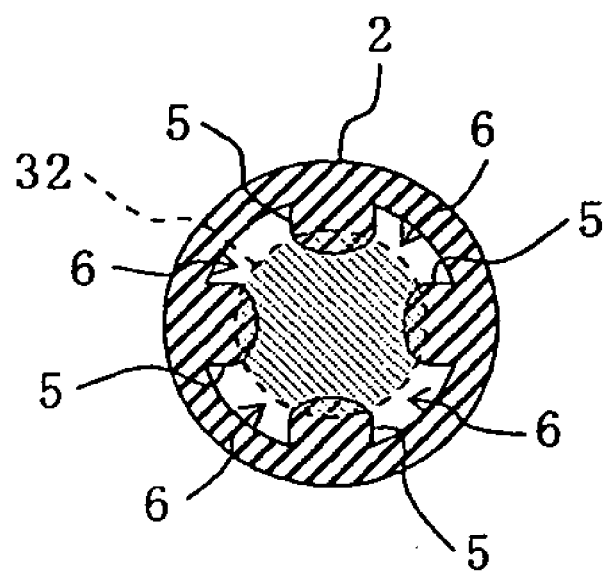

To avoid such an inconvenience, the plural bump-shaped locking stoppers 5 and 5 are formed so as to protrude from some parts of the internal wall surface of the leading-end case portion 2. Accordingly, as FIG. 4B shows, even when the power receiving portion 32 pulled toward the base-end portion side of the catheter main body 1 is brought into contact with the locking stoppers 5 and 5, the retrieval channel 6 is not closed completely. Part of the retrieval channel 6 corresponding to the outside of the power receiving portion 32 is left unclosed. For this reason, the fragments of the blood clot BC can be securely sucked and retrieved through the retrieval passage 6.

Besides, it is preferable that, in this embodiment, at least a part of the leading-end case portion 2 or at least a part of the object cutting means 3 be made of a metal member. Such a use of metal makes the position of the leading end of the catheter main body 1 observable by means of an X-ray image.

As has been described thus far, the blood clot BC is cut, in this embodiment, by means of the cutting portion 31 of the object cutting means 3 exposed through the opening 4 formed in the leading-end case portion 2. In this event, when the opening 4 is brought into contact with the blood clot BC at the beginning of the cutting operation, the blood clot BC is pulled into the leading-end case portion 2 through the opening 4 by the negative pressure produced in the lumen 11. In addition, the power receiving portion 32 is pulled toward the side of the base-end portion of the catheter main body 1 by the negative pressure produced in the lumen 11, and the cutting portion 31 is stretched out. The cutting portion 31 thus stretched out cuts the blood clot BC, and the fragment of the cut blood clot BC are immediately sucked into the leading-end case portion 2, by the negative pressure produced in the lumen 11, through the opening 4 and the retrieving opening that is a gap formed in the cutting portion 31.

Accordingly, the blood clot BC can be retrieved and removed easily and smoothly from the blood vessel BV while all the fragments of the cut blood clot BC are sucked into the leading-end case portion 2 without allowing any of the fragments to flow away. In addition, the cutting portion 31 cuts only a part of the blood clot BC corresponding to the cutting portion 31 of the object cutting means 3 exposed through the opening 4. Accordingly, the cutting and the suction of the blood clot BC can be carried out safely without damaging the other parts, such as the internal wall of the blood vessel BV.

In addition, the object cutting means 3 (the cutting portion 31) in this embodiment is made to move back and forth by adjusting the sucking force produced by the driving means. When the strong negative pressure in the lumen 11 is made weaker, the restoring force of the spring elasticity inherent in the cutting portion 31 contracts the cutting portion 31 back to its original length. While the cutting portion 31 is restoring the original length, the cutting portion 31 cuts the blood clot BC. The fragments of the blood clot BC thus cut out are immediately sucked, by the negative pressure produced in the lumen 11, into the leading-end case portion 2 through the opening 4 and the retrieving opening that is a gap formed in the cutting portion 31.

Accordingly, the blood clot BC can be cut and removed efficiently by the repeating of the back-and-forth motion including an action for the stretching-out of the cutting portion 31 and an action for the contracting of the cutting portion 31 until the restoration of its original length. In addition, the opening 4 is formed in the leading-end inclined face 21, which is the obliquely-formed leading-end portion of the leading-end case portion 2. Accordingly, even when the circumferential body portion of the suction catheter 10 cannot be inserted so as to face the blood clot BC, the cutting and the removing of the blood clot BC can be carried out, little by little, starting from the edge portion of the blood clot BC.

Second Embodiment

The suction catheter of the present invention can be modified for the purpose of allowing the suction catheter to be efficiently inserted into the blood vessel and of allowing the leading end of the suction catheter to reach the lesion (the blood clot) easily. To put it differently, a suction catheter of this second embodiment differs from the suction catheter of the above-described first embodiment in that the suction catheter of the second embodiment is provided with means for assisting the insertion of suction catheter.

Incidentally, when each of the following embodiments is described, the description to be given focuses mainly on the points that differ between each of the following embodiments and the above-described first embodiment. For those constituent parts that are common to each of the following embodiments and the above-described first embodiment, the same reference numerals that are used in the first embodiment will be given in each of the following embodiments. No description will be given for those common constituent parts. To put it differently, those constituent parts that will not be described specifically in the following embodiments can be assumed to be the same as those counterparts described in the first embodiment.

Figure 5:
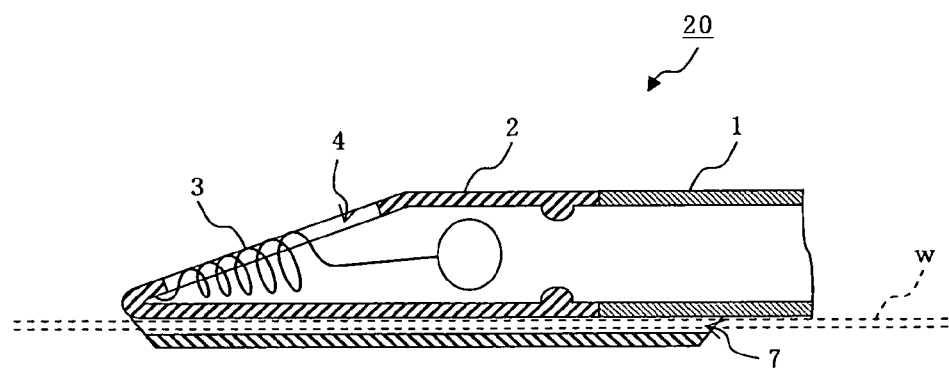
FIG. 5 is a schematic sectional view illustrating a suction catheter according to a second embodiment of the present invention.

As FIG. 5 shows, a suction catheter 20 according to this second embodiment includes: a catheter main body 1; a leading-end case portion 2 positioned at a leading-end portion 1a of the catheter main body 1; and object cutting means 3 installed in the leading-end case portion 2. In addition, a guide-wire hole 7 is formed in the outer surface of at least one of the catheter main body 1 and the leading-end case portion 2. A guide wire W is inserted into the guide-wire hole 7. The suction catheter 20 is provided with the guide-wire hole 7 that serves as means for assisting the insertion of suction catheter and that formed along the longitudinal-axis direction of the suction catheter 20.

As has been described above, in this embodiment, the guide wire W that has been beforehand placed in the blood vessel is inserted into the guide-wire hole 7, and the suction catheter 20 is inserted along the guide wire W. The guide-wire hole 7 is thus used as the means for assisting the insertion of suction catheter. Accordingly, the suction catheter 20 can be efficiently inserted into the blood vessel.

Third Embodiment

The suction catheter of the present invention can be modified for the purpose of allowing the driving means to give the power that is not the sucking force to the object cutting means. To put it differently, a suction catheter of this third embodiment differs from the suction catheter of the above-described first embodiment in that the suction catheter of this third embodiment is provided with driving means that is not a suction apparatus.

Figure 6:
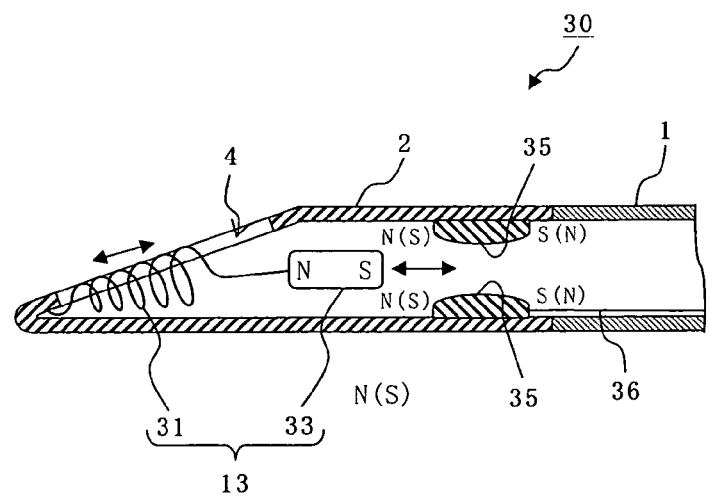
FIG. 6 is a schematic sectional view illustrating a suction catheter according to a third embodiment of the present invention.

As FIG. 6 shows, a suction catheter 30 according to this third embodiment includes: a catheter main body 1; a leading-end case portion 2 positioned at a leading-end portion 1a of the catheter main body 1; and object cutting means 13 installed in the leading-end case portion 2.

The object cutting means 13 is made, either partially or entirely, of a magnetic material, and includes, for example, a cutting portion 31 exposed through an opening 4 and a power receiving portion 33. The power receiving portion 33 moves the cutting portion 31 when a magnetic force is applied to the power receiving portion 33 from outside.

The power receiving portion 33 may be made of a permanent magnet. The permanent magnet used for this purpose may be a ferrite magnet or a rare-earth magnet. In other words, a permanent magnet of any kind may be used for this purpose.

The driving means of this third embodiment is a magnetic-force apparatus that is capable of attracting or repelling the power receiving portion 33 by means of the magnetic force.

An example of the magnetic apparatus is an apparatus including an electromagnet 35 provided to the internal wall of the leading-end case portion 2 and a power-supply source that supplies electricity to the electromagnet 35 via an electric wire 36. The electromagnet 35 is capable of generating a magnetic force temporarily when energized. The electromagnet 35 is also capable of reverse the magnetic polarities when the direction of the electric current supplied to the electromagnet 35 is reversed.

As has been described above, in this embodiment, the magnetic force (attractive magnetic field) generated by the energized electromagnet 35 attracts the power receiving portion 33 to the electromagnet 35. When the electromagnet 35 ceases to be energized, the magnetic force also ceases to be generated, and the object cutting means 13 is made to be attracted to an internal leading end 2a of the leading-end case portion 2 by the spring biasing force inherent in the cutting portion 31. In this way, the power is given to the object cutting means 13 in this third embodiment. Alternatively, the power can be given to the object cutting means 13 by attracting the power receiving portion 33 to the electromagnet 35 and by repelling the power receiving portion 33 from the electromagnet 35 while the polarity of the electromagnet 35, that is, the direction of the electric current applied for energizing the electromagnet 35 is repeatedly reversed. To put it differently, the power can be given to the object cutting means 13 by the generation of an attractive magnetic field and a repulsive magnetic field, which is accomplished by reversing the direction of the electric current applied to the electromagnet 35.

Accordingly, the suction catheter 30 of this third embodiment is capable of moving the object cutting means 13 back and forth without weakening the sucking force used for retrieving the fragments of the blood clot.

Fourth Embodiment

The suction catheter of the present invention can be modified for the purpose of allowing the opening that is to be brought into contact with the blood clot to face in a different direction. To put it differently, a suction catheter of this fourth embodiment differs from the suction catheter of the above-described first embodiment in that the opening of this fourth embodiment is formed at a position that is different from the position of its counterpart of the first embodiment.

Figure 7:
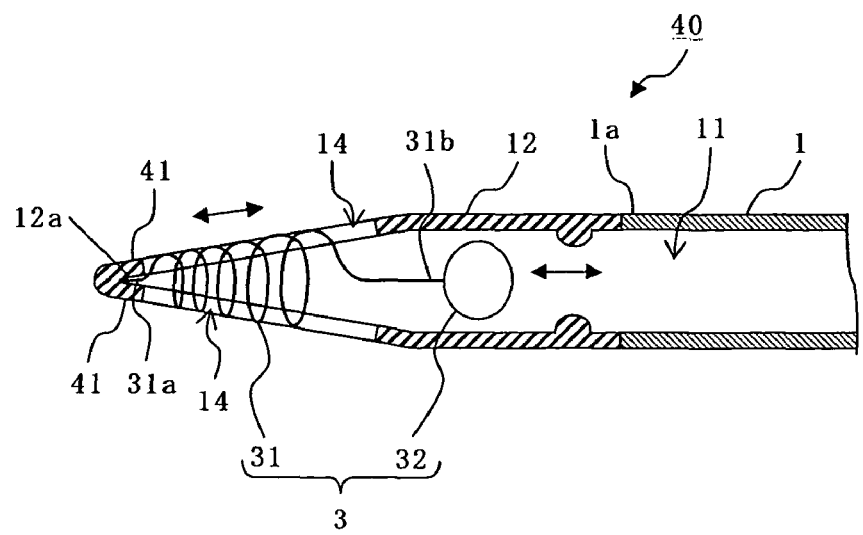
FIG. 7 is a schematic sectional view illustrating a suction catheter according to a fourth embodiment of the present invention.

As FIG. 7 shows, a suction catheter 40 according to this fourth embodiment includes: a catheter main body 1; a leading-end case portion 12 positioned at a leading-end portion 1a of the catheter main body 1; and object cutting means 3 installed in the leading-end case portion 12.

Plural openings 14 and 14 to retrieve the blood clot are formed in the leading-end case portion 12. The openings 14 and 14 also serve as the inlets through which the blood clot is sucked into the vacuumed lumen 11 of the catheter main body 1. Accordingly, each of the openings 14 and 14 is formed so as to face the blood clot that sticks to the internal wall of the blood vessel.

As FIGS. 7 shows, the leading-end case portion 12 has a conical surface 41 that is formed so as to gradually reduce its diameter toward the leading end of the leading-end case portion 12, and the openings 14 and 14 are formed in the conical surface 41. Note that the conical surface mentioned here may be a surface formed so as to uniformly reduce its diameter toward the leading end of the leading-end case portion 12, or may be an arc-shaped surface formed so as to reduce its diameter with a degree of reduction increasing toward the leading end of the leading-end case portion 12.

The leading-end case portion 12 may be formed either integrally with or separately from the catheter main body 1.

Parts of the object cutting means 3 are exposed through the openings 14 and 14, respectively. In addition, the object cutting means 3 is movable in the axial direction within the leading-end case portion 12.

The object cutting means 3 includes, for example, a cutting portion 31 that is exposed through the openings 14 and 14, and a power receiving portion 32 which receives the power from outside and which moves the cutting portion 31.

In FIG. 7, the cutting portion 31 is illustrated as a spiral-shaped body (coil-spring shape). The spiral-shaped cutting portion 31 has a first end 31a fixed to the proximity of an internal leading end 12a of the leading-end case portion 12, and a second end 31b provided with the power receiving portion 32.

Figure 8:
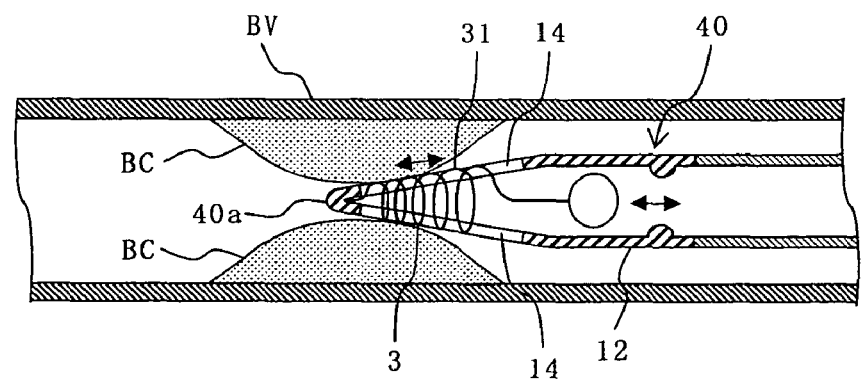
FIG. 8 is a schematic sectional view illustrating the state where an object (a blood clot) is cut and removed by means of the suction catheter according to the fourth embodiment shown in FIG. 7.

What will be described next is a way of cutting and removing a blood clot in a blood vessel by means of the suction catheter 40 with the above-described configuration. FIG. 8 is a schematic sectional diagram illustrating a way of cutting and removing a blood clot by means of a suction catheter.

Firstly, as FIG. 8 shows, the suction catheter 40 is inserted into a blood vessel BV until a leading-end side 40a of the suction catheter 40 reaches the position of a blood clot BC. Then, the cutting portion 31 of the object cutting means 3 exposed through the openings 14 and 14 of the leading-end case portion 12 is brought into contact with the blood clot BC. In the meanwhile, the base-end portion of the suction catheter 40 is connected to a suction apparatus. Subsequently, the lumen 11 is vacuumed by means of the suction apparatus, and the object cutting means 3 is made to move back and forth. The blood clot BC in the blood vessel BV can thus be cut by the cutting portion 31, and the fragments of the blood clot BC can be sucked in and then retrieved.

As has been described thus far, in this fourth embodiment, the plural openings 14 and 14 are formed in the conical surface 41 of the leading-end case portion 12 formed so as to gradually reduce its diameter toward the leading end. Accordingly, the suction catheter 40 of this fourth embodiment can be placed so as to face the blood clot BC formed in the blood vessel BV and sticking to the internal wall of the blood vessel BV in every direction. In addition, the cutting and the removing of the blood clot BC thus formed and sticking to the internal wall in every direction can be carried out without turning the suction catheter 40 that has been placed in the blood vessel BV. Accordingly, the use of the suction catheter 40 of this fourth embodiment eliminates the possibility of harming the inside of the blood vessel BV with the turning action that would be necessary otherwise.

Fifth Embodiment

The suction catheter of the present invention can be modified for the purpose of allowing the opening that is to be brought into contact with the blood clot to face in a still different direction. To put it differently, a suction catheter of this fifth embodiment differs from the suction catheters of the above-described first and the fourth embodiments in that the opening of this fifth embodiment is formed at a position that is different from the position of its counterpart of any of the first and the fourth embodiments.

Figure 9:
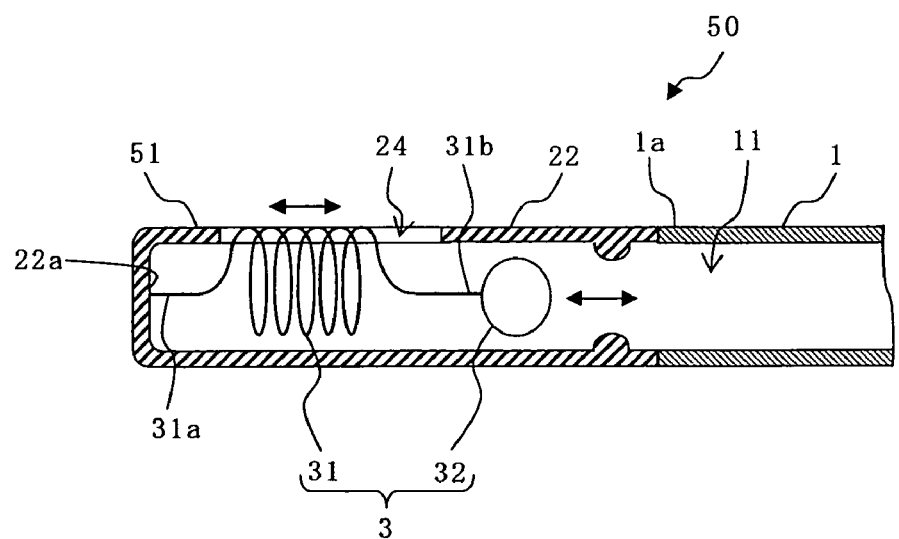
FIG. 9 is a schematic sectional view illustrating a suction catheter according to a fifth embodiment of the present invention.

As FIG. 9 shows, a suction catheter 50 according to this fifth embodiment includes: a catheter main body 1; a leading-end case portion 22 positioned at a leading-end portion 1a of the catheter main body 1; and object cutting means 3 installed in the leading-end case portion 22.

An opening 24 is formed in the leading-end case portion 22, and the blood clot is retrieved through the opening 24. The opening 24 also serves as the inlet through which the blood clot is sucked into a vacuumed lumen 11 of the catheter main body 1. Accordingly, the opening 24 is formed so as to face the blood clot that sticks to the internal wall of the blood vessel.

As FIG. 9 shows, an end portion of the leading-end case portion 22 is formed in a cylindrical shape to be a leading-end-side circumferential-body surface 51, and the opening 24 is formed in the leading-end-side circumferential-body surface 51.

The leading-end case portion 22 may be formed either integrally with or separately from the catheter main body 1.

A part of the object cutting means 3 is exposed through the opening 24. In addition, the object cutting means 3 is movable in the axial direction within the leading-end case portion 22.

The object cutting means 3 includes, for example, a cutting portion 31 that is exposed through the opening 24, and a power receiving portion 32 which receives the power from outside and which moves the cutting portion 31.

In FIG. 9, the cutting portion 31 is illustrated as a spiral-shaped body (coil-spring shape). The spiral-shaped cutting portion 31 has a first end 31a fixed to the proximity of an internal end 22a of the leading-end case portion 22, and a second end 31b provided with the power receiving portion 32.

Figure 10:
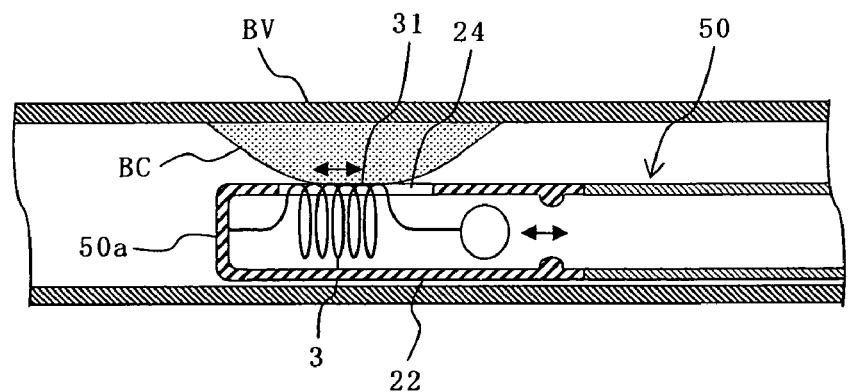
FIG. 10 is a schematic sectional view illustrating the state where an object (a blood clot) is cut and removed by means of the suction catheter according to the fifth embodiment shown in FIG. 9.

What will be described next is a way of cutting and removing a blood clot in a blood vessel by means of the suction catheter 50 with the above-described configuration. FIG. 10 is a schematic sectional diagram illustrating a way of cutting and removing a blood clot by means of a suction catheter.

Firstly, as FIG. 10 shows, the suction catheter 50 is inserted into a blood vessel BV until a leading-end side 50a of the suction catheter 50 reaches the position of a blood clot BC. Then, the cutting portion 31 of the object cutting means 3 exposed through the opening 24 of the leading-end case portion 22 is brought into contact with the blood clot BC. In the meanwhile, the base-end portion of the suction catheter 50 is connected to a suction apparatus. Subsequently, the lumen 11 is vacuumed by means of the suction apparatus, and the object cutting means 3 is made to move back and forth. The blood clot BC in the blood vessel BV can thus be cut by the cutting portion 31, and the fragments of the blood clot BC can be sucked in and then retrieved.

As has been described thus far, in this fifth embodiment, the opening 24 is formed in the cylindrical-shaped leading-end-side circumferential-body surface 51 of the leading-end case portion 22. Accordingly, the suction catheter 50 of this fifth embodiment can be placed parallel with the wall surface of the blood vessel BV. Accordingly, the cutting and removing of the blood clot can be progressed from the inner side of the blood vessel BV towards the wall surface of the blood vessel BV.

Sixth Embodiment

The suction catheter of the present invention can employ other types of object cutting means. To put it differently, a suction catheter of this sixth embodiment differs from the suction catheter of the above-described first embodiment in the structure of the object cutting means of the suction catheter.

Figure 11:
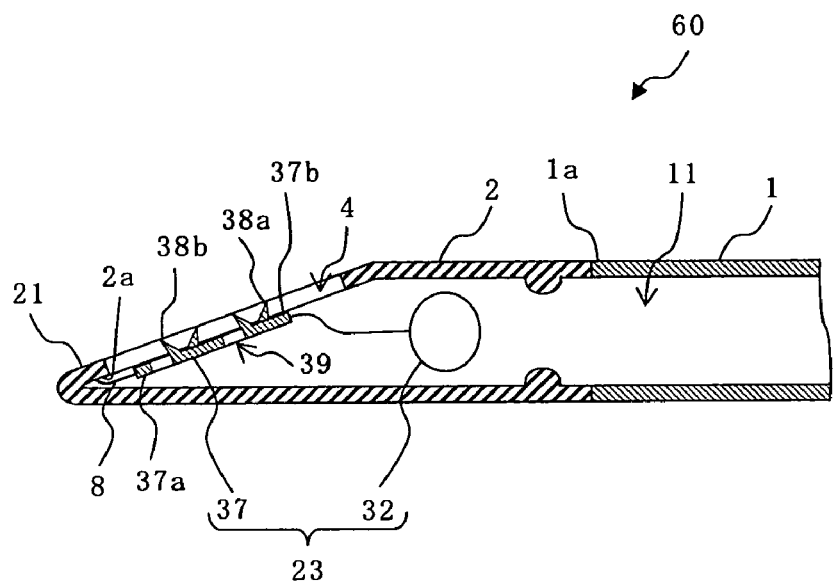
FIG. 11 is a schematic sectional view illustrating a suction catheter according to a sixth embodiment of the present invention.

As FIG. 11 shows, a suction catheter 60 according to this sixth embodiment includes: a catheter main body 1; a leading-end case portion 2 positioned at a leading-end portion 1a of the catheter main body 1; and object cutting means 23 installed in the leading-end case portion 2.

An opening 4 is formed in the leading-end case portion 2, and the blood clot is retrieved through the opening 4. The opening 4 also serves as the inlet through which the blood clot is sucked into the vacuumed lumen 11 of the catheter main body 1. Accordingly, the opening 4 is formed so as to face the blood clot that sticks to the internal wall of the blood vessel.

As FIG. 11 shows, the leading-end portion of the leading-end case portion 2 is formed obliquely to be a leading-end inclined face 21, and the opening 4 is formed in the leading-end inclined face 21.

The leading-end case portion 2 may be formed either integrally with or separately from the catheter main body 1.

A part of the object cutting means 23 is exposed through the opening 4. In addition, the object cutting means 23 is movable in the axial direction within the leading-end case portion 2. Note that "the axial direction" mentioned here is the same direction as the direction of the longitudinal axis of the catheter main body 1.

The object cutting means 23 includes, for example, a plate-shaped cutting portion 37 that is exposed through the opening 4, and a power receiving portion 32 which receives the power from outside and which moves the plate-shaped cutting portion 37.

Figure 12:
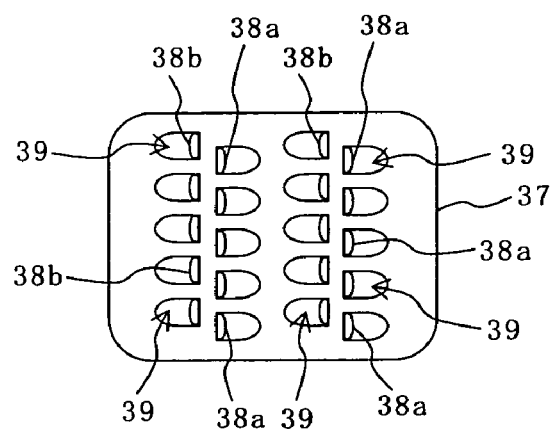
FIG. 12 is a schematic plan view illustrating object cutting means of the suction catheter according to the sixth embodiment shown in FIG. 11.
Figure 13:
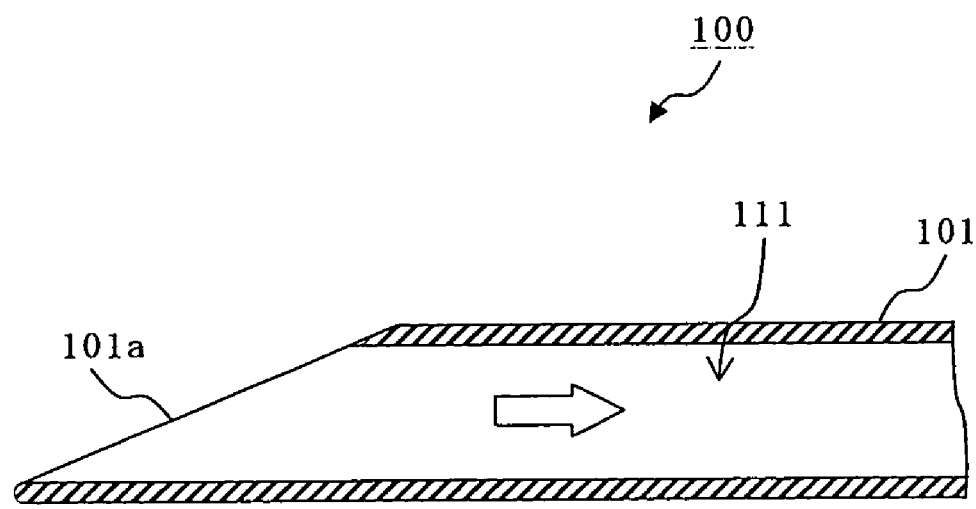
FIG. 13 is a schematic sectional view illustrating a conventional suction catheter.

The plate-shaped cutting portion 37 includes two kinds of protruding pieces 38a and 38a as well as 38b and 38b. The protruding pieces 38a and 38a as well as 38b and 38b are raised up in directions toward the side where the opening 4 is placed. The plate-shaped cutting portion 37 also includes retrieving openings 39 and 39. The fragments of the blood clot cut off by the protruding pieces 38a and 38a as well as 38b and 38b are taken into the inside of the leading-end case portion 2 through the retrieving openings 39 and 39. The plate-shaped cutting portion 37 can be formed in a grater shape. For example, as FIG. 12 shows, plural cuts each of which has a tongue shape are, firstly, made in the surface of a plate-shaped member. Then, the portions of the cuts thus made are raised up in directions toward the side where the opening 4 is placed. Thus, plural pairs of a retrieving opening 39 and either a protruding piece 38a or a protruding piece 38b can be formed while each the retrieving openings 39 is formed at the base of the corresponding one of the protruding pieces 38a and 38a as well as 38b and 38b.

Of the two kinds of protruding pieces 38a and 38a as well as 38b and 38b, the first protruding pieces 38a and 38a work when the object cutting means 23 moves from the leading-end side to the rear-end side of the leading-end case portion 2. In contrast, the second protruding pieces 38b and 38b work when the object cutting means 23 moves from the rear-end side to the leading-end side of the leading-end case portion 2 so as to restore the original position.

FIG. 11 shows that the plate-shaped cutting portion 37 has a first end 37a connected to a stretchable member 8 that is fixed to the proximity of an internal leading end 2a of the leading-end case portion 2. FIG. 11 also shows that the power receiving portion 32 is provided at a second end 37b of the plate-shaped cutting portion 37. The stretchable member 8 has a stretching function to allow the object cutting means 23 to move back and forth.

As has been described thus far, the blood clot BC is cut, in this sixth embodiment, by means of the plate-shaped cutting portion 37 of the object cutting means 23 exposed through the opening 4 formed in the leading-end case portion 2. Accordingly, the blood clot BC can be fractured into fine fragments of the blood clot BC, and then removed. The fragments thus removed can be efficiently retrieved by being sucked into the leading-end case portion 2 through the opening 4.

The present invention is industrially useful in an industry that employs suction catheters used, in a treatment, by being inserted into a blood vessel for the purpose of sucking and removing an object, such as a blood clot. The present invention is particularly important in the market of suction catheters used for sucking and removing a blood clot formed in the arteries of the brain or of the heart as well as in the arteries and the veins of the four limbs.

What is claimed is:

1. A suction catheter made of a flexible lengthy body with a lumen formed therein, and used in a treatment where a leading-end side of the suction catheter is adapted to be inserted into a blood vessel, where a base-end portion is connected to a suction apparatus, and where the lumen is vacuumed by means of the suction apparatus adapted to suck out and retrieve an object in the blood vessel, the suction catheter comprising:
 a catheter main body made of the flexible lengthy body;
 a leading-end case portion positioned at a leading-end portion of the catheter main body and including an opening for retrieving the object; and
 object cutting means that is partially exposed through the opening, and is movable in the axial direction within the leading-end case portion,
 wherein the object cutting means includes:
  a cutting portion with a cutting area made of a wire-like member provided so as to traverse in a substantially perpendicular direction to the axial direction;
  a power receiving portion that is connected to the cutting portion, and moves the cutting portion in the axial direction when the power receiving portion receives power from outside, and while the object cutting means is in operation, the object that sticks to an internal wall of the blood vessel is cut off, at the opening of the leading-end case portion, by means of the cutting area of the cutting portion.

2. The suction catheter according to claim 1, wherein the cutting portion is a spiral body formed by winding up the wire-like member a number of times.

3. The suction catheter according to claim 1 or 2, wherein the leading-end case portion includes a locking stopper formed in an internal wall of the leading-end case portion, the locking stopper restricting a movement of the object cutting means toward the base-end portion of the catheter main body.

4. The suction catheter according to claim 1 or 2, wherein any one of at least a part of the leading-end case portion and at least a part of the object cutting means is made of a metal member.

5. The suction catheter according to claim 1 or 2, wherein the opening is formed in a leading-end inclined face of an obliquely-formed leading-end portion of the leading-end case portion.

6. The suction catheter according to claim 1 or 2, wherein the opening is formed in a leading-end-side circumferential-body surface of the leading-end case portion.

7. The suction catheter according to claim 1 or 2, wherein at least one of the catheter main body and the leading-end case portion includes a guide-wire hole formed in the outer surface thereof, the guide-wire hole allowing a guide wire to be inserted thereinto.

8. A suction-catheter system comprising:
 the suction catheter according to claim 1 or 2; and
 driving means for supplying power to the object cutting means included in the suction catheter.

9. The suction-catheter system according to claim 8, wherein the driving means is capable of adjusting the strength of the power supplied to the object cutting means.

10. The suction-catheter system according to claim 8,
 wherein the object cutting means includes a stretchable member that enables the object cutting means to move back and forth in response to the change in the strength of the power supplied by the driving means, and
 the driving means is a suction apparatus that attracts the object cutting means by means of a sucking force.

11. The suction catheter according to claim 1, wherein the leading-end case portion has a wall extending from a proximal end to a distal end, wherein said opening extends distally along the wall, and wherein the cutting portion is exposed through the opening and remains at least partially within the leading-end case portion during axial movement during a cutting operation so that suction and cutting occur concurrently on the object within the opening.

12. The suction catheter according to claim 1, wherein the leading-end case portion has an inclined face, and wherein said opening extends along the inclined face proximal to a distal tip of the leading-end case portion.

13. The suction catheter according to claim 12, wherein the cutting portion is anchored to a distal end of the leading-case portion during a cutting operation.

14. The suction catheter according to claim 1, wherein the cutting portion moves axially within the leading-end case portion during a cutting operation between a first configuration in which the cutting portion spans a first length within the opening proximal to the distal end and a second configuration in which the cutting portion spans a second length, greater than the first length, within the opening proximal to the distal end.

15. The suction catheter according to claim 1, wherein the object cutting means has a first end at which is the cutting portion and a second end at which is the power receiving portion, wherein both the cutting portion and power receiving portion are situated in the leading-end case portion, an entirety of the leading-end portion adapted to be inserted inside the blood vessel.

16. The suction catheter according to claim 1,
wherein the cutting portion is positioned within the opening and is adapted to cut a portion of the object within the path of the cutting portion within the opening during a cutting operation so that cutting of the object and suctioning to retrieve a cut portion of the object occur concurrently within at least a volume within the leading-end case portion bordered by a plane of the opening.

17. A suction catheter made of a flexible lengthy body with a lumen formed therein, and used in a treatment where a leading-end side of the suction catheter is adapted to be inserted into a blood vessel, where a base-end portion is connected to a suction apparatus, and where the lumen is vacuumed by means of the suction apparatus adapted to suck out and retrieve an object in the blood vessel, the suction catheter comprising:
a catheter main body made of the flexible lengthy body;
a leading-end case portion positioned at a leading-end portion of the catheter main body and including an opening for retrieving the object; and
object cutting means that is partially exposed through the opening, and is movable in the axial direction within the leading-end case portion,
wherein the object cutting means includes:
a cutting portion with a cutting area made of a wire-like member provided so as to traverse in a substantially perpendicular direction to the axial direction;
a power receiving portion that is connected to the cutting portion, and moves the cutting portion in the axial direction when the power receiving portion receives power from outside, and
while the object cutting means is in operation, the object that sticks to an internal wall of the blood vessel is cut off, at the opening of the leading-end case portion, by means of the cutting area of the cutting portion; and
wherein the power receiving portion is made of a magnetic material, and the leading-end case portion includes magnetic-force generating means for supplying power to the power receiving portion, the magnetic-force generating means being provided to the internal wall of the leading-end case portion.

18. The suction catheter according to claim 17, wherein the cutting portion is a spiral body formed by winding up the wire-like member a number of times.

19. A suction-catheter system comprising a suction catheter and a driving means, the suction catheter made of a flexible lengthy body with a lumen formed therein, and used in a treatment where a leading-end side of the suction catheter is adapted to be inserted into a blood vessel, where a base-end portion is connected to a suction apparatus, and where the lumen is vacuumed by means of the suction apparatus adapted to suck out and retrieve an object in the blood vessel, the suction catheter comprising:
a catheter main body made of the flexible lengthy body;
a leading-end case portion positioned at a leading-end portion of the catheter main body and including an opening for retrieving the object; and
object cutting means that is partially exposed through the opening, and is movable in the axial direction within the leading-end case portion,
wherein the object cutting means includes:
a cutting portion with a cutting area made of a wire-like member provided so as to traverse in a substantially perpendicular direction to the axial direction;
a power receiving portion that is connected to the cutting portion, and moves the cutting portion in the axial direction when the power receiving portion receives power from outside, and
while the object cutting means is in operation, the object that sticks to an internal wall of the blood vessel is cut off, at the opening of the leading-end case portion, by means of the cutting area of the cutting portion;
wherein the driving means supplies power to the object cutting means included in the suction catheter; and
wherein at least a part of the object cutting means is made of a magnetic material, and
the driving means is a magnetic-force apparatus that attracts or repels the object cutting means by means of a magnetic force.

20. The suction catheter according to claim 19, wherein the cutting portion is a spiral body formed by winding up the wire-like member a number of times.

\* \* \* \* \*